US00PP15114P2

(12) United States Plant Patent
Walden et al.

(10) Patent No.: US PP15,114 P2
(45) Date of Patent: Aug. 31, 2004

(54) FLORIBUNDA ROSE PLANT NAMED 'JACMOUSE'

(50) Latin Name: *Rosa hybrida*
Varietal Denomination: JACmouse

(75) Inventors: John K. Walden, Loomis, CA (US); Keith W. Zary, Somis, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/697,612

(22) Filed: Oct. 29, 2003

(51) Int. Cl.[7] ..... A01H 5/00
(52) U.S. Cl. ..... Plt./143
(58) Field of Search ..... Plt./143

*Primary Examiner*—Anne Marie Grunberg
*Assistant Examiner*—S. B. McCormick-Ewoldt
(74) *Attorney, Agent, or Firm*—Klarquist Sparkman LLP

(57) ABSTRACT

Floribunda rose plant having unique flower color; compact, vigorous floribunda plant habit; dark green disease resistant foliage; and ability to grow vigorously on its own roots.

1 Drawing Sheet

Genus and species: *Rosa hybrida.*
Variety denomination: 'JACmouse'.

ORIGIN OF THE INVENTION

The present invention relates to a new and distinct variety of a floribunda rose plant named 'JACmouse' which was originated by us by crossing the variety 'MORsegold,' a miniature, U.S. Plant Pat. No. 6,617, with the variety 'JACpoy,' also a miniature, U.S. Plant Pat. No. 9,015.

BACKGROUND OF THE INVENTION

The primary objective of this breeding was to produce a new rose variety having the large vigorous plant habit of the female parent combined with the bright colors of the male parent. A miniature was expected but both parents are very vigorous and 'JACmouse' is a floribunda selected from plants grown from the cross.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which We are aware:

1. Unique flower color;
2. Compact, vigorous floribunda plant habit;
3. Dark green disease resistant foliage; and
4. Ability to grow vigourously on its own roots.

Asexual reproduction of this new variety by cuttings, as performed at Wasco, Calif., shows that the foregoing and all other characteristics and distinctions come true to form and are established and transmitted through succeeding propagations.

COMPARISON WITH PARENTS

The subject variety differs from the female and male parents of the cross in larger flower size (8–9 cm vs. 5–6 cm in diameter), and plant size (70–80 cm vs. 30–40 cm in length) and in flower color (yellow and pink with a yellow reverse vs. a yellow orange and pink blend).

COMPARISON WITH SIMILAR VARIETY

The subject variety differs in that there is not a rose of which we are aware with anything even similar in flower color.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of our new rose cultivar with color descriptions using terminology in accordance with The Royal Horticultural Society (London) Colour Chart (2001), except where ordinary dictionary significance of color is indicated.

Parentage:
*Seed parent.*—'MORsegold' (U.S. Plant Pat. No. 6,617).
*Pollen parent.*—'JACpoy' (U.S. Plant Pat. No. 9,015).

FLOWER

Observations made from plants grown in a garden environment at Somis, Calif. commencing at one and one half years of age over a ten month period after winter dormancy.

Blooming habit: Continuous.
Bud:
*Size.*—About 3 cm long and 1.8 cm in diameter when the petals start to unfurl.
*Form.*—The bud form is long.
*Color.*—When sepals first divide, bud color is Red Group 47A with Yellow Group 2C spot at the base and Greyed-Purple Group 184A at the apex. When half blown, the upper sides of the inner petals are Orange Group 24B, the outer petals being Red Group 52A; and the lower sides of the inner petals are Yellow-Orange Group 23C, the outer petals being Red Group 55A. Sepals: Color: Upper surface: Yellow-Green Group 146D at the base, Greyed-Red Group 182A being the prominent color with a tinge of White Group N155A on margins. Lower surface: Yellow-Green Group 144B at the base, Greyed-Red Group 181A being the prominent color with an occasional tinge of White Group N155A on margins. Length: 22–28 mm. Width: 8–10 mm. Shape: Subulate. Surface texture: Upper surface: Canescent. Lower surface: Glandular. There are three lightly appendaged sepals. There are two unappendaged sepals with ciliolate edges.

*Receptacle.*—Color: Yellow-Green Group 144A. Shape: Funnel. Size: Medium, about 7 mm long×9 mm wide. Surface: Smooth.

*Peduncle.*—Length: Short, averaging about 30–40 mm. Surface: Glandular. Color: Yellow-Green Group 144A at the top turning Greyed-Red Group 182 on the majority. Strength: Erect.

Bloom:

*Size.*—Medium. Average open diameter is about 7.5 cm.

*Borne.*—In pyramidal clusters of 3–5 blooms.

*Stems.*—Strength: Normal. Average length is about 12 cm with a diameter of 3–5 mm.

*Form.*—When first open: High centered. Permanence: Outer petal edges curl slightly.

*Petalage.*—Number of petals under normal conditions: 30–35.

*Color.*—The outer petals on their upper surface are Yellow Group 12A at their base shading to Orange-Red Group 32B in the mid-portion, thence to Red Group 54B with the apex of the petal being Red Group 53C. On their lower surface the outer petals are Yellow Group 12C at their base, thence shade to Orange Group 28C, the top half being Red Group 48C. The major color on the upper side is Orange-Red Group 30D.

*Variegations.*—The lower surfaces have a Yellow Group 12C vein in center of petal from base to apex.

*Discoloration.*—The general tonality at the end of the first day: Orange-Red Group 30D. At the end of the third day: Red Group 48B. By day seven color fades to Red Group 48D and by day nine petals drop.

*Fragrance.*—None.

Petals:

*Texture.*—Thick.

*Shape.*—Between obovate and obdeltoid.

*Surface.*—Smooth, glabrous.

*Margin.*—Entire. Apex Shape: Cuspidate. Base Shape: Cuneate.

*Form.*—Edges slightly recurved.

*Arrangement.*—Imbricated.

*Petaloids.*—Number: 3–5 Color: Orange Group 28B with Yellow Group 12A at the base.

*Persistence.*—Petals drop off cleanly before drying.

*Lastingness.*—On the plant: Fair (about 5 days). As a cut flower: Fair (about 7 days).

Reproductive parts:

*Stamens.*—Number: 120–130. Length: 11–15 mm. Anthers: Length: 2–3 mm. Color: Yellow Group 13A. Filaments: Color: Yellow Group 13A. Length: 9–12 mm. Pollen: Color: Yellow Orange Group 22A.

*Pistils.*—Number: 60–70. Length: 7–8 mm. Styles: Color: Yellow Group 1C. Length: 6–7 mm. Stigmas: Color: Yellow Group 2C. Length: 1 mm.

*Hips.*—None observed.

PLANT

*Form.*—Bush.

*Growth.*—Vigorous, upright, branching, compact.

*Age at maturity.*—2 years.

*Mature plant.*—Height: 70–80 cm. Width: 50–60 cm.

*Rootstock.*—Own root.

Foliage: Number of leaflets on normal mid-stem leaves: Generally 7, occasionally 5.

*Size.*—Medium about 11 cm long×8 cm wide.

*Quantity.*—Abundant.

*Color.*—New foliage: Upper side: Greyed Red Group 178A. Lower side: Greyed Red Group 178A. Old foliage: Upper side: Green Group 136A. Lower side: Green Group N 138A, often with a blush of Greyed Red Group 178A on leaf edges.

Leaflets:

*Size.*—About 4 cm long×2 cm wide.

*Shape.*—Pointed oval.

*Base shape.*—Aequilateral.

*Apex shape.*—Acuminate.

*Texture.*—Leathery, glossy.

*Edge.*—Serrated.

*Serrations.*—Single, small.

*Petiole.*—Color: Yellow Green 146D.

*Petiole rachis.*—Color: Yellow Green 146D. Underside: Rough with prickles.

*Auricle shape, if present.*—None.

*Stipules.*—Length: 12 mm. Surface: Serrated, bearded. Shape: Adnate.

*Disease resistance.*—Resistant to mildew and rust and susceptible to blackspot under normal growing conditions.

*Pest resistance.*—Not tested.

*Vein color.*—Green Group N 138A.

*Venation pattern.*—Reticulate.

Wood:

*New wood.*—Color: Greyed Purple Group 183D. Bark: Smooth.

*Old Wood.*—Color: Green Group 146A. Bark: Smooth.

Prickles:

*Quantity.*—On main canes from base: Ordinary. On laterals from main canes: Ordinary.

*Form.*—Hooked downward.

*Length.*—5–7 mm.

*Color when young.*—Greyed Red Group 184B.

*Color when mature.*—Greyed Orange Group 174B.

Small prickles:

*Quantity.*—On main stalks: None. On laterals: None.

Winter hardiness. Hardy to zone 5.

I claim:

1. A new and distinct variety of rose plant of the floribunda class, substantially as herein shown and described, characterized particularly by unique flower color; compact, vigorous floribunda plant habit; dark green, disease resistant foliage; and ability to grow vigorously on its own roots.

* * * * *

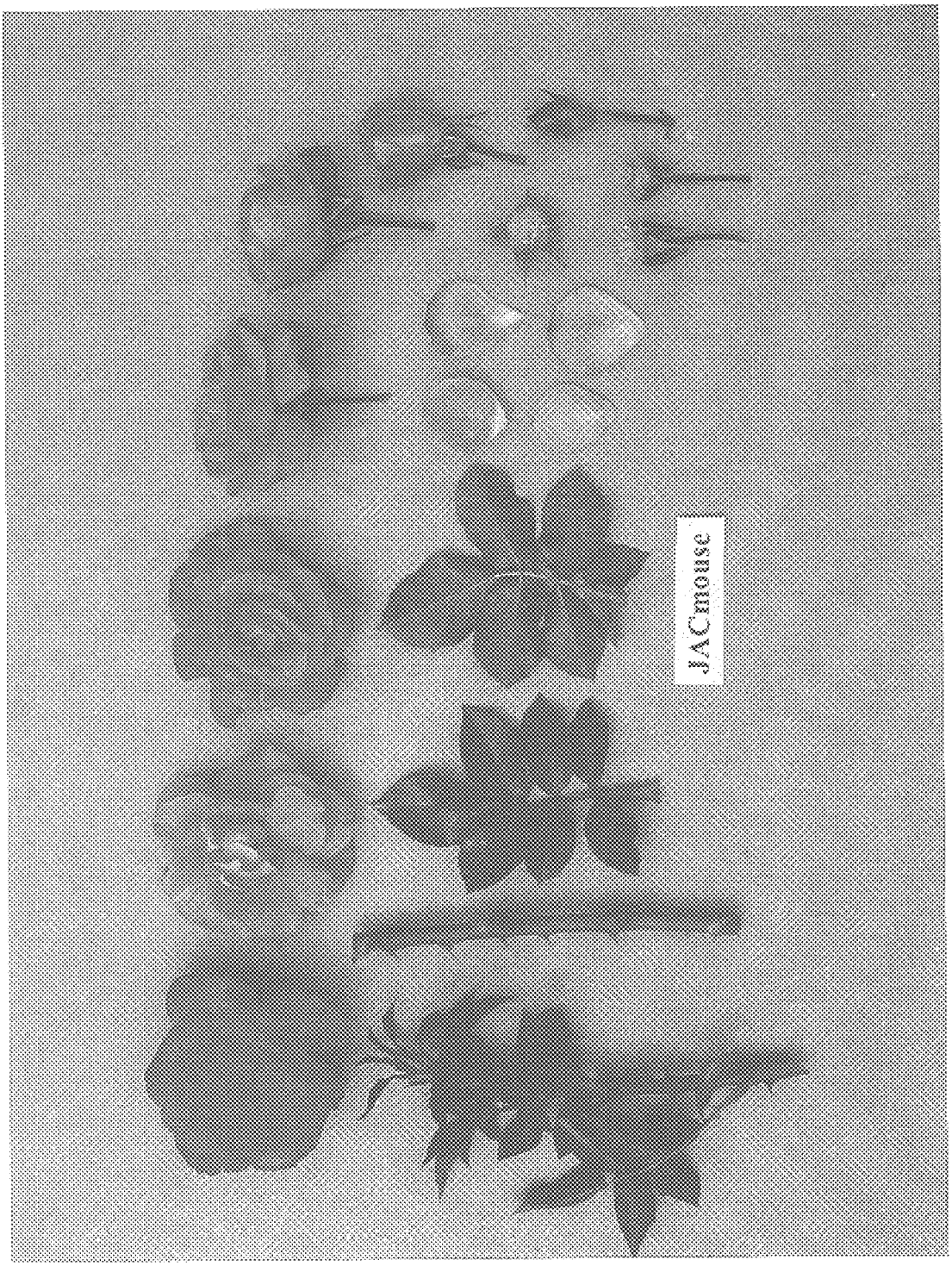
JACmouse